United States Patent [19]

Graham

[11] Patent Number: 4,990,137
[45] Date of Patent: Feb. 5, 1991

[54] CLOSED WOUND DRAINAGE SYSTEM WITH CLEARING PORT AND METHOD FOR STERILE CLEARING OF CLOSED WOUND DRAINAGE SYSTEM

[75] Inventor: Dennis Graham, Woodhaven, N.Y.

[73] Assignee: Memorial Hospital for Cancer and Allied Diseases, New York, N.Y.

[21] Appl. No.: 212,902

[22] Filed: Jun. 29, 1988

[51] Int. Cl.[5] .............................................. A61M 1/06
[52] U.S. Cl. ........................................ 604/73; 604/319
[58] Field of Search ............................... 128/760, 764; 608/73-76, 118, 119, 86, 48, 51, 317, 319-321

[56] References Cited

U.S. PATENT DOCUMENTS

| | | | |
|---|---|---|---|
| 3,115,138 | 12/1963 | McElvenny et al. | 128/278 |
| 3,376,868 | 4/1968 | Mondiadis | 128/278 |
| 3,742,952 | 7/1973 | Magers et al. | 128/278 |
| 3,752,158 | 8/1973 | Kariher | 128/278 |
| 3,880,164 | 4/1975 | Stepno | 604/131 |
| 3,889,677 | 6/1975 | Nehring | 128/278 |
| 3,998,227 | 12/1976 | Holbrook et al. | 604/319 |
| 4,376,439 | 3/1983 | Lauterjung | 128/276 |
| 4,416,661 | 11/1983 | Norman et al. | 604/86 |
| 4,429,693 | 2/1984 | Blake et al. | 604/133 |
| 4,474,575 | 10/1984 | Eckenhoff et al. | 604/131 |
| 4,559,035 | 12/1985 | Benjamin et al. | 604/73 |
| 4,708,717 | 11/1987 | Deane et al. | 604/35 |
| 4,828,552 | 5/1989 | Malette | 604/319 |

OTHER PUBLICATIONS

Byers, "Pilot Study Using a Portable, Battery-Operated Suction Drainage System in Head and Neck Surgery (1986)", Surgidyne Vari Dyne Vacuum Controller brochure, Mar. 1986.
Argyle Brand, "Urinary Drainage Bag" operating instructions (undated).
Con Med Corporation, "Pleura-Gard" Chest Drainage System brochure, Jan. 1987.
Snyder Hemovac Instructions 8/1/76.
Snyder Hemovac Craniotomy Instructions 6/79.
Snyder Urevac Instructions 6/79.
Snyder Hemovac Craniotomy Kit.

*Primary Examiner*—Randall L. Green
*Assistant Examiner*—Randy Shay
*Attorney, Agent, or Firm*—John P. White

[57] ABSTRACT

The present invention relates to a closed wound drainage system with a clearing port connected to the system, having a permeable membrane for sealable passage of a needle therethrough for injection of fluid into the system in order to flush the system without opening the system. The clearing port may also be used to withdraw fluid samples from the system for laboratory analysis without contaminating the system or the sample during the withdrawal procedure. The present invention also relates to a method for sterile clearing of obstructions in a closed wound drainage system.

13 Claims, 1 Drawing Sheet

CLOSED WOUND DRAINAGE SYSTEM WITH CLEARING PORT AND METHOD FOR STERILE CLEARING OF CLOSED WOUND DRAINAGE SYSTEM

BACKGROUND OF THE INVENTION

This invention relates generally to closed body wound drainage devices and particularly, to methods and apparatus for clearing obstructions from closed wound drainage devices of the type having suction source connected to a closed container and a suction line connected to the suction source, for withdrawing fluid from a body wound.

Patient wounds, including surgery sites, often generate excess body fluids, which must be drained from the wound for proper patient healing. Wounds should be drained in a manner which minimizes the likelihood of contamination and infection. In order to prevent wound infection, sterile, closed wound drainage systems, that prevent environmental contact with the wound or the system, are often used by health-care practitioners.

Sterile, closed wound drainage systems generally have a suction source connected to a sealed container, which receives the drained body fluid and a suction line connected to the container. Known examples of suction sources in closed wound drainage systems include inflatable balloons or other types of bladders in generally rigid, sealed containers; compressible, biased bladders or vacuum lines. The suction line, or a device connected to the suction line, such as a suction catheter, is routed to the wound site for receipt of the drainage fluid. Many closed wound drainage devices have a one-way check valve between the container and the suction line, which allows drainage fluid flow from the suction line to the container but prevents flow from the container to the suction line. Examples of known, closed wound drainage systems include the devices shown in U.S Pat. Nos. 3,742,952; 3,752,158; 3,889,677 and 4,559,035. Closed wound drainage systems that are actually marketed included the DAVOL ® brand models CWS 400 and RELIAVAC TM, as well as the Snyder brand HEMOVAC ® evacuators. Many known closed wound drainage systems are presterilized, disposable units.

In use, closed wound drainage systems tend to clog with obstructions created by the drainage fluid, thereby reducing system efficiency. In extremely clogged systems, the unit can no longer evacuate fluid from the patient's wound, leading to wound complications.

Past attempts to remove system obstructions by removing the suction line from the patient, opening the system and cleaning the system components were unsatisfactory, because opening the system violated system sterility and increased risks of patient infection complications. The other known alternative of discarding and replacing clogged drainage systems with new ones prevented infection but was expensive. Accordingly, there has been a long-felt need by health-care practitioners for a closed wound drainage system that can be cleared to remove obstructions without compromising system sterility.

Health-care practitioners often want to withdraw samples of wound drainage fluids for laboratory analysis. The only known way to obtain fluid samples from closed wound drainage systems is to open the sealed container and empty fluid from the container. Fluid emptied from the container is exposed to the atmosphere and may be contaminated by microorganisms that do not inhabit the system. Also, microorganisms may enter the container portion during the emptying procedure and subsequently grow therein, but they may not enter the suction line. Thus, laboratory analysis of fluid withdrawn from the container may not accurately indicate which microorganisms, if any inhabit the wound site or the drainage system suction line.

It is an object of the present invention to create a closed wound drainage system that is clearable to remove internal obstructions in the system without opening the system.

It is also an object of the present invention to create a closed wound drainage system from which wound fluids can be withdrawn without opening the system.

SUMMARY OF THE INVENTION

These objects have been attained with the closed wound drainage system of the present invention which can be cleared internally to remove obstructions without opening the system and exposing it to the atmosphere Wound fluids samples can also be withdrawn without contaminating either the system or the sample.

The present invention relates to a closed wound drainage system for sterile drainage of body fluids from a patient without exposing the wound to the atmosphere comprising a closed container for receipt of body fluids from a patient; suction means for creating a partial vacuum in the container; a suction line connected to the container for passage of body fluids therethrough into the container; and a clearing port connected to the system, having a permeable membrane for sealable passage of a syringe needle therethrough for injection of fluid into the system, so as to flush the system without opening the system to the atmosphere.

The present invention also relates to a closed wound drainage system for sterile drainage of body fluids from a patient comprising a closed container for receipt of body fluids from a patient; a suction source connected to the container for creating a partial vacuum in the container; valve means for allowing entry of fluid into the container and preventing exhaust of fluid from the container; a suction line connected to the valve means for passage of body fluids therethrough into the container; and a clearing port connected to the suction line, having a permeable membrane for sealable passage of a syringe needle therethrough for injection of fluid into the suction line towards the container, so as to flush the system without opening the system to the atmosphere.

The present invention also relates to a method for sterile clearing of obstructions in a closed wound drainage system of the type having a closed container, a suction source connected to the container and a suction line connecting the container and a patient's wound comprising sealably inserting a syringe needle into the system through a permeable membrane on the system; directing the inserted needle towards the obstruction; injecting fluid into the system with the syringe, so as to flush the obstruction into the container; and removing the syringe and needle from the permeable membrane.

DETAILED DESCRIPTION OF THE INVENTION

The present invention includes a closed wound drainage system for sterile drainage of body fluids from a patients comprising a closed container for receipt of body fluids from a patient; suction means for creating a partial vacuum in the container; a suction line connected to the container for passage of body fluids therethrough into the container; and a clearing port connected to the system, having a permeable membrane for sealable passage of a syringe needle therethrough for injection of fluid into the system, so as to flush the system without opening the system to the atmosphere.

The present invention also includes a closed wound drainage system for sterile drainage of body fluids from a patient comprising a closed container for receipt of body fluids from a patient; a suction source connected to the container for creating a partial vacuum in the container; valve means for allowing entry of fluid into the container and preventing exhaust of fluid from the container; a suction line connected to the valve means for passage of body fluids therethrough into the container; and a clearing port connected to the suction line, having a permeable membrane for sealable passage of a syringe needle therethrough for injection of fluid into the suction line towards the container, so as to flush the system without opening the system to the atmosphere.

In the system, the clearing port may be connected to the suction line so that fluid exhausted from a syringe passed through the permeable membrane is generally directed towards the valve means.

The clearing port may include a manifold with an outlet connected to the suction line, with the permeable membrane connected to the manifold coaxially and in fluid communication with the outlet and at least one inlet connected to the manifold and in fluid communication with the outlet. The manifold may also have a pair of inlets generally converging towards the outlet with the permeable membrane between the inlets.

Suction source may be an inflatable bladder in a generally rigid container; a compressible, biased bladder; a vacuum line or a reciprocable piston pump.

The present invention includes a method for sterile clearing of obstructions in a closed wound drainage system of the type having a closed container, a suction source connected to the container and a suction line connecting the container and a patient's wound comprising sealably inserting a syringe needle into the system through a permeable membrane on the system; directing the inserted needle towards the obstruction; injecting fluid into the system with the syringe, so as to flush the obstruction into the container; and removing the syringe and needle from the permeable membrane.

The following examples are illustrative of the closed wound drainage system and method for sterile cleaning of obstructions in closed wound drainage systems of the present invention, but they are in no way intended to restrict the scope of the claims hereto.

Figure 1:
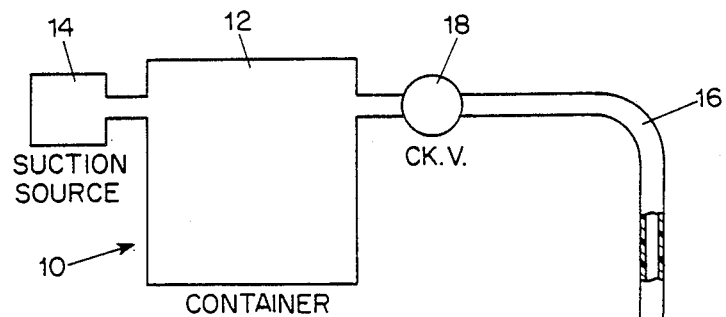
FIG. 1 is a schematic view of a closed wound drainage system with clearing port of the present invention.

As shown in FIG. 1, the closed wound drainage system 10 of the present invention has a closed container 12 connected to a suction source 14, which generates a pressure less than ambient atmospheric pressure.

Figure 3:
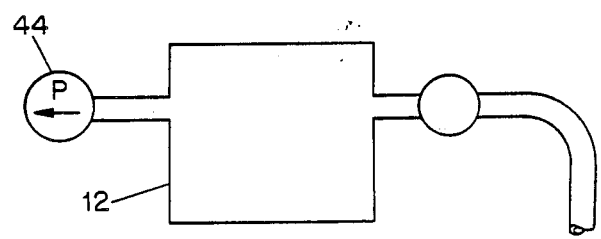
FIG. 3 is a schematic view of a closed wound drainage system of the present invention showing a vacuum pump suction source.
Figure 4:
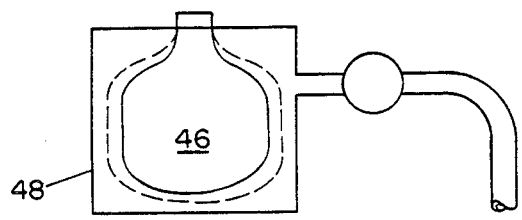
FIG. 4 is a schematic view of a closed wound drainage system of the present invention showing an inflatable bladder suction source in a generally rigid container.
Figure 6:
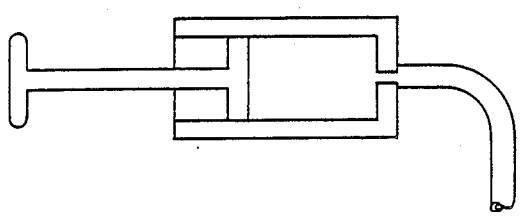
FIG. 6 is a schematic view of a closed wound drainage system of the present invention showing reciprocable piston pump suction source.
Figure 5:
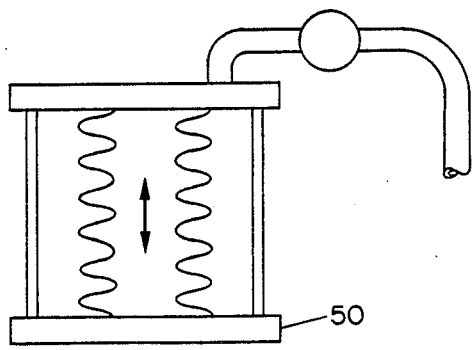
FIG. 5 is a schematic view of a closed wound drainage system of the present invention showing a compressible, biased bladder suction source.

The suction source may include a power driven vacuum pump 44, shown in FIG. 3, an inflatable balloon 46 or other bladder within a generally rigid container 48, as shown in FIG. 4, biased bladders, including a spring-biased bladder 50, as shown in FIG. 5, squeeze bulbs, reciprocable piston pumps 52, as shown in FIG. 6 (including syringes) or any other suction source for closed wound drainage systems known to those skilled in the art. Examples of such known closed wound drainage systems with suction sources are shown in U.S. Pat. Nos. 3,742,852; 3,754,158; 3,889,667 and 4,559,035, the teachings of which are incorporated herein by reference.

The system 10 has a suction line 16, one end of which is connected to the container 12 and the other end of which is routed to the patient's wound site. Alternatively, the other end of the suction line 16 may be connected to another drainage device, such as suction catheter, that is in turn routed to the patient's wound site.

Desirably, the system 10 has a check valve 18 between the container 12 and the suction line 16, which allows fluid flow from the suction line into the container, but prevents fluid flow from the container to the suction line to prevent drained fluid from returning to the patient,.s wound site However, the check valve 18 is not required to practice the present invention.

In use, the suction line 16 and check valve 18 can develop obstructions caused, for example by coagulation and hardening of the patient's drained body fluids. Obstructions inhibit the system 10 from draining fluid from the patient's wound site and in severe cases, completely block the system.

In order to clear obstructions in the system 10 it has a clearing port 20, shown attached to suction line 16, for clearing obstructions without opening the system. Thus, obstructions can be cleared without compromising system sterility. As shown in FIG. 1, the clearing port 20 has a permeable membrane 22 for sealable passage of a syringe needle therethrough (not shown). Desirably, the clearing port 20 is oriented so that the syringe needle is directed towards the check valve 18 and container 12, so that a stream of fluid exhausted from the syringe will be directed towards the downstream suction line and valve, rather than the wound.

While FIG. 1 shows only a single clearing port 20 connected to the suction line 16, multiple clearing ports may be connected to the system 10. At least one clearing port located on the suction line is advantageous, because it allows simultaneous flushing of the suction line and the check valve 18 It may be desirable to incorporate another clearing port into the check valve or in close proximity thereto for localized clearing of the valve.

Figure 2:
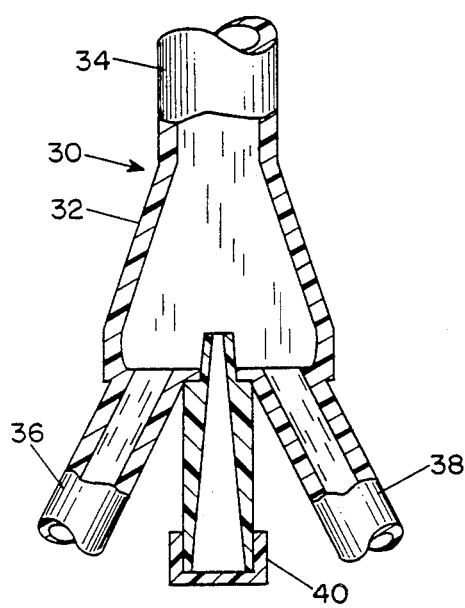
FIG. 2 is a partial view of another embodiment of a clearing port of the closed wound drainage system of the present invention.

FIG. 2 shows another embodiment of a clearing port 30 having a manifold 32 with an outlet 34 that is connected to the suction line portion which runs to the container. The manifold 32 has at least one inlet for coupling to the patient's wound, and as shown in FIG. 2 there is a pair of inlets 36, and 38 which are in fluid communication with and converge toward the outlet 34. Either or both of inlets 36 and 38 may be coupled to the patient's wound site and they may be selectively used for fluid flow by blocking fluid flow with a valve or clamp. The manifold 32 has a permeable membrane 40 that is coaxial with the outlet 34, so that a syringe needle passed therethrough can inject fluid directly through the outlet centerline. As shown in FIG. 2, the membrane 40 is located between the converging inlets 36 and 38.

When a health-care practitioner wants to clear an obstruction from the closed wound drainage system of the present invention, shown in FIG. 1, the practitioner inserts the needle of a sterile syringe containing a sterile fluid, such as saline solution, through a clearing port 20 permeable membrane 22 and injects the fluid into the suction line 16 The injected fluid stream breaks up the obstruction After completing the injection, the needle is withdrawn from the self-sealing, permeable membrane 22 and the system remains unexposed to the atmosphere, to preserve sterility. The injection procedure may be repeated as often as necessary in as many clearing ports that are connected to the system. Periodic drainage system clearing may be performed in order to prevent obstruction formation. As can be appreciated by health-care practitioners, it is desirable to record how much clearing fluid is injected into the system, so that the fluid volume actually drained from the patient's wound can be monitored.

A health-care practitioner can also use the clearing port 20 to withdraw a wound fluid sample from the suction line 16 with a syringe for laboratory analysis Both the drainage system and the withdrawn sample remain free from atmospheric contamination.

What is claimed is:

1. A closed wound drainage system for sterile drainage of body fluids from a patient comprising:
    a closed container for receipt of body fluids from a patient;
    a suction line connected to the container having an end for placement in fluid communication with the patient for passage of body fluids therethrough into the container; and
    a clearing port connected in continuous open fluid communication with the suction line proximal the patient would end and distal the container, the clearing port having a permeable membrane for sealable passage of a syringe needle therethrough for injection of fluid into the suction line towards the container, so as to flush the system without opening the system to atmosphere.

2. A closed wound drainage system for sterile drainage of body fluids from a patient comprising:
    a closed container for receipt of body fluids from a patient;
    a suction source connected to the container for creating a partial vacuum in the container;
    a valve means for allowing entry of fluid into the container and preventing exhaust of fluid form the container;
    a suction line connected to the valve means having an end for placement in fluid communication with the patient for passage of body fluids therethrough into the container; and
    a clearing port connected in continuous open fluid communication with the suction line proximal the patient would ned and distal the container, the clearing port having a permeable membrane for sealable passage of a syringe needle therethrough for injection of fluid into the suction line towards the container, so as to flush the system without opening the system to the atmosphere or disrupting fluid communication between the patient wound and the container.

3. The closed wound drainage system of claim 2, wherein the clearing port is connected to the suction line so that fluid exhausted from a syringe passed through the permeable membrane is generally directed towards the valve means.

4. The closed wound drainage system of claim 3, wherein the clearing port has a manifold with an outlet connected to the suction line, the permeable membrane is connected to the manifold coaxially and in fluid communication with the outlet and at least one inlet connected to the manifold and in fluid communication with the outlet.

5. The closed wound drainage system of claim 4, wherein the manifold has a pair of inlets generally converging towards the outlet and the permeable membrane is between the inlets.

6. The closed wound drainage system of claim 4, wherein the manifold is constructed of material which resists penetration of the syringe needle.

7. The closed wound drainage system of claim 2, wherein the suction source is an inflatable bladder in the container and the container is generally rigid.

8. The closed wound drainage system of claim 2, wherein the suction source is a compressible, biased bladder forming at least part of the container.

9. The closed wound drainage system of claim 2, wherein the suction source is a vacuum line.

10. The closed wound drainage system of claim 2, wherein the suction source is a reciprocable piston pump.

11. A method for sterile clearing of obstructions in a closed wound drainage system of the type having a downstream closed container, a suction source connected to the container and a suction line connecting the container and an upstream patient's wound comprising:
    sealably inserting a syringe needle into the system through a permeable membrane located upstream of the obstruction and in continuous open fluid communication with the suction line;
    directing the inserted needle downstream toward the obstruction;
    injecting fluid into the system with the syringe, so as to flush the obstruction downstream into the container; and
    removing the syringe and needle form the permeable membrane.

12. The method of claim 11, wherein the permeable membrane is located proximal the patient wound end and distal the container.

13. The method of claim 11, wherein the permeable membrane is connected to a manifold that is in fluid communication with the suction line constructed of a material which resists penetration of the needle.

* * * * *